United States Patent [19]

Sorbi et al.

[11] Patent Number: 4,797,480
[45] Date of Patent: Jan. 10, 1989

[54] NEW BIOLOGICALLY ACTIVE FLUORESCENT CYCLIC NUCLEOTIDES

[75] Inventors: Robert T. Sorbi; Antonio Caretta; Andrea Cavaggioni; Liliana Marchesi Gastaldi, all of Parma, Italy

[73] Assignee: Universita Degli Studi di Parma, Parma, Italy

[21] Appl. No.: 866,354

[22] Filed: May 23, 1986

[30] Foreign Application Priority Data

Jun. 6, 1985 [IT] Italy ................. 42506 A/85

[51] Int. Cl.$^4$ .................. C07H 19/10; C07H 19/20
[52] U.S. Cl. .................................. 536/27; 536/28; 536/29
[58] Field of Search ................... 536/27, 28

[56] References Cited

U.S. PATENT DOCUMENTS 3,712,885  1/1973  Weimann et al. .
3,988,442  10/1976  Cehouic ................... 536/27
4,369,181  1/1983  Miller et al. ................... 536/27

OTHER PUBLICATIONS

Miller et al., Am. Chem. Soc., (1973) 12, 5310.
Antonio Caretta et al., "Binding Stoichiometry of a Fluorescent cGMP Analogue to Membranes of Retinal Rod Outer Segments", 1985, Eur. J. Biochem., 153(1), pp. 49–53.

Primary Examiner—Ronald W. Griffin
Assistant Examiner—Jenny Tou
Attorney, Agent, or Firm—Parkhurst, Oliff & Berridge

[57] ABSTRACT

Sybthesis of new biologically active fluorescent cyclic nucleotides of general formula:

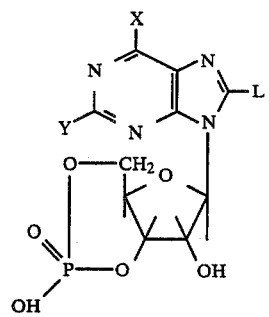

wherein X=OH and Y=NH$_2$ or X=NH$_2$ and Y=H and L is a fluorescent group of the class of 5 (or 6)-thioacetamido-fluorescein or of 5(or 8)-(2 thioacetamido-ethyl)-amino-naphthalene -1-sulphonic acid.

11 Claims, No Drawings

NEW BIOLOGICALLY ACTIVE FLUORESCENT CYCLIC NUCLEOTIDES

In biochemical research there is an increasing use of natural products rendered fluorescent by the addition of a fluorophore because they enable molecular events to be visualised within a minimum concentration, quantity and time domain. Furthermore; the role of cyclic nucleotides of the following type:

(1) guanosine-3',5'-(cyclic) phosphate

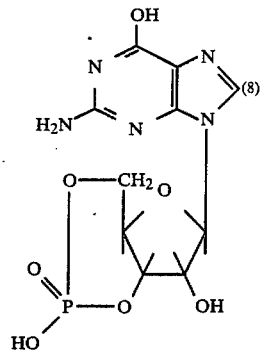 (I)

(2) adenosine-3',5'-(cyclic) phosphate

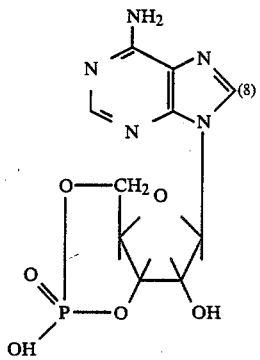 (II)

in regulating cell metabolism has been increasingly receiving the attention of researchers. Our intention was to produce fluorescent cyclic nucleotides which were biologically active. We took as our starting point the fact that cyclic nucleotides substituted in position 8 of the base do not lose activity (Muneyama et al., Biochemistry 12, 2390–2395, 1971). We therefore sought to attach in this position a known fluorophore, namely a fluorescein or a naphthalene-sulphonic dye. The formers can be determined at very low concentrations and are not subject to interference with UV-absorbent products, and the latters are unsurpassed reporter molecules sensitive to the polarity of the environment around the molecule. Moreover, energy can be transferred between the two fluorochromes. For this purpose, we reacted a sulphydryl group introduced into position 8 of the nucleotide with sulphydryl-fluorescent reagents. The unknown factor was whether substituting with groups of such high molecular weight made the derivative inactive towards cell regulatory systems based on the binding of cyclic nucleotides to particular proteins. The object of the present research was the synthesis of said fluorescent cyclic nucleotides and their biological characterisation.

These can be formulated starting from a cyclic nucleotide of formula (I) or (II) by substituting the hydrogen atom in position 8 by a group which is a derivative radical of 5-(thioacetamido)-fluorescein class

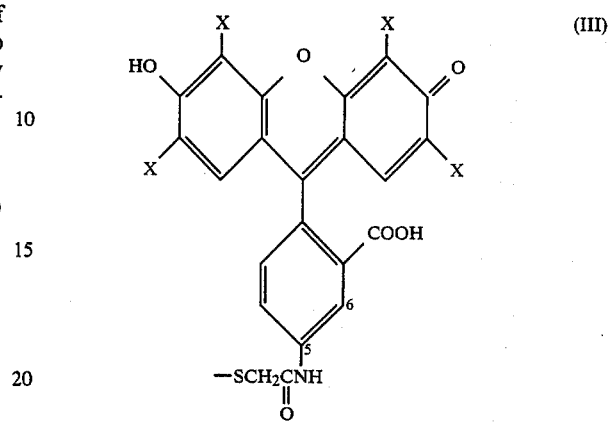 (III)

where x is H, Br or I (fluorescein, eosin, erythrosyn respectively) or of its isomer 6-(thioacetamido)-fluorescein (IV) or which is a derivative radical of 5-(2-thioacetamido-ethyl)-amino-naphthalene-1-sulphonic acid

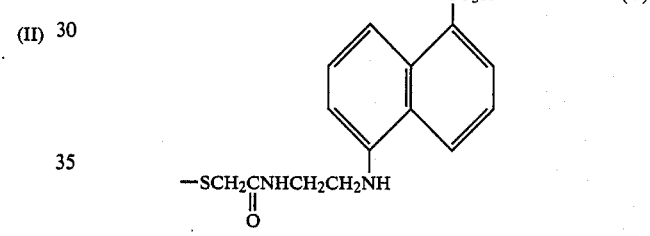 (V)

or of the corresponding isomer 8-(2-thioacetamido-ethyl)-amino-naphthalene-1-sulphonic acid (VI).

The obtained products are represented by the general formula:

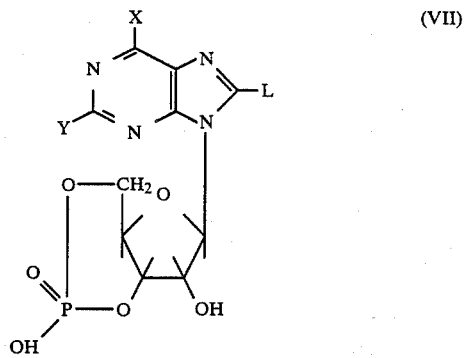 (VII)

wherein $X=OH$ or $NH_2$, Y is $NH_2$ when $X=CH$ and is H when $X=NH_2$, and L represents the fluorescent group bound through a thioacetamido linkage to the nucleotide. The synthesis proceeds by successive stages: firstly, bromination of the cyclic nucleotides in position 8 of the nucleotide and purification by chromotography or another method; secondly, substituting the bromine with a sulphydryl by reaction with thiourea in an alkaline environment; thirdly, reacting with a compound of the fluorescein class able to react with the sulphydryl group such as 6 (or 5)-iodoacetamido-fluorescein, or with 5 (or 8)-(2-iodoacetamido-ethyl)-amino-naphtalene-1-sulphonic acid.

By this means, HI is eliminated and the fluorescent group is inserted into position 8. The product is then purified. The reactions are conducted at ambient temperature and take place in a minimum of red light to enable the operations to proceed. The biological characterisation was effected by three tests, namely an activity, a binding and a hydrolysis resistance test. The activity test consists of determining the ability of the new fluorescent compounds to activate the permeability of retinal rod membranes (Caretta and Caravaggioni, Eur. J. Biochem, 132, 1–8, 1983). Briefly, the calcium flux into vesicles of retinal rod outer segment membranes filled with Arsenazo III was determined by complexometry. The flux was determined spectrophotometrically at a wavelength of 652 nm immediately after adding one of the following fluorescent cyclic nucleotides:

Compound (1) guanosine derivative of formula (I) containing the fluorescein class radical formula (III) in position 8

Compound (2) guanosine derivative of formula (I) containing the 5-(2-thioacetamido-ethyl-amino)-naphthalene-1-sulphonic acid radical of formula (V) in position 8

Compound (3) adenosine derivative of formula (II) containing the fluorescein class radical of formula (III) in position 8

Compound (4) adenosine derivative of formula (II) containing the 5-(2-thioacetamido-ethyl-amino)-naphthalene-1-sulphonic acid radical of formula (V) in position 8.

Compounds 1, 2, 3, and 4 were all active.

The active concentration for the cyclic substituted with groups of the fluorescein class was 100 times less than for the respective natural cyclic nucleotides. Consequently, the activity of these new fluorescent cyclic nucleotides is approximately 100 times greater than the activity of the natural cyclic nucleotides from which they derive. The binding test at equilibrium under dialysis measures the ability of the fluorescent compounds to bind in retinal rod membranes to the sites to which natural cyclic nucleotides bind. Briefly, the test was carried out by bringing vesicles of retinal rod membranes into equilibrium under dialysis with a balancing solution containing concentrations of compound 1) varying from 0.2 to 12 micromolar. The excess fluorescent cyclic nucleotide bound to the membranes was determined by sampling, measuring the fluorescence of the membranes and comparing with the balancing solution. Taking account of the required corrections, it was found that the new fluorescent cyclic nucleotide (compound 1) binds to said sites with micromolar affinity (see Caretta, et al.—Enz. J. Biochem.—(1985)—15-3—pag. 45/53).

Finally, the hydrolysis test measures the molecule stability under experimental conditions. Briefly, the fluorescent cyclic nucleotides were exposed to a retinal rod homogenate for a time sufficient to ensure total hydrolysis of the respective natural cyclic nucleotides to monoesters. The result demostrated that the new fluorescent cyclic nucleotides are resistant to hydrolysis and that the fluorescence remains associated with the cyclic nucleotide.

Concluding, the simple and specific synthesis of fluorescent cyclic nucleotides (compound 1, 2, 3 and 4), their high biological activity towards biochemical regulatory systems which are based on the binding of cyclic nucleotides, and finally their stability under experimental conditions; make these new molecules useful in biochemical and pharmacological research, and enable them to be produced industrially.

EXAMPLE 1

Synthesis of 8-(5-thioacetamido-fluorescein)-guanosine-3',5'-(cyclic) phosphate 0.135 g of 8-bromo-guanosine-3',5'-(cyclic) phosphate (pyridunium salt) and 0.075 g of thiourea in 3 ml of methanol were left overnight at room temperature. 0.06 g of sodium methylate, 3 ml of water and 0.110 g of 5-iodoacetamido-fluorescein (Molecular Probes, Junction City, OR 79448, USA) were then added in succession, followed by 0.2N NaOH to neutralise the solution. After one hour the product was separated by thin layer chromatography on silica gel with an acid solvent A (butanol, acetone, water, acetic acid, ammonia 350/250/250/142/8 v/v).

The fluorescent band with Rf=0.75 was eluted with methanol, and the methanol was flash-evaporated leaving 0.15 g of solid product. Rf in solvent A 0.75, in solvent B (isopropanol), water, ammonia 7/2/1 v/v) 0.45. Spectrum in water at pH 9; absorbance maxima at 492 nm, 250 nm shoulders at 260 nm, 290 nm.

Fluorescence excitation maximum at 492 nm in alkaline water, emission maximum at 520 nm. Stable in darkness under dry conditions.

EXAMPLE 2

The process of example 1 was repeated but using 6-iodoacetamido-fluorescein instead of 5-iodoacetamido-fluorescein. The isomer obtained has same properties as the compound of Example 1.

EXAMPLE 3

Synthesis of 8-[5(2)iodoacetamido-ethyl)-amino-naphthalene-1-sulphonic acid]-guanosine-3',5'-(cyclic)phosphate The process is the same as in Example 1, but substituting the iodo-acetamido-fluorescein with 5-(2-iodoacetamido-ethyl)-amino-naphthalene-2-sulphonic acid (Hudson and Weber, 1973 Biochemistry 12, 4154) and working in dim red light. Rf in solvent A 0.48, in solvent B 0.45.

Spectrum in methanol: absorbance maxima at 340 nm, 258 nm, absorbance minima at 320 nm, 238 nm, shoulder at 270 nm. It decomposes in light.

EXAMPLE 4

The process of Example 3 was repeated but using 8-(2-iodo-acetamido-ethyl)-amino-naphthalene-1-sulphonic acid. The isomer obtained has the same properties as the compound of Example 3.

EXAMPLE 5

The process of Example 1 was repeated but substituting 8-bromo-adenosine-3',5'-(cyclic) phosphate for 8-bromo-guanosine-3',5'-(cyclic) phosphate.

The obtained product 8-(5-thioacetamido-fluorescein)-adenosine-3',5'-(cyclic) phosphate has the same Rf values and the same spectrum as the compound obtained in Example 1.

EXAMPLE 6

The process of Example 3 was repeated but substituting 8-bromo-adenosine-3',5'-(cyclic) phosphate for 8-bromo-guanosine-3',5'-(cyclic) phosphate.

The obtained product 8-[5-(2-thiacetamido-ethyl)-amino-naphthalene-1-sulphonic acid]-adenosine-3',5'-(cyclic)phosphate has the same Rf values and the same spectrum as the compound obtained in Example 3.

EXAMPLE 7

Synthesis of 8-(5-thioacetamido-fluorescein)-5')monophosphate-guanosine

The working conditions of Example 1 were applied, but substituting 8-bromo-phosphate-guanosine for 8-bromo-3',5'-(cyclic) phosphate-guanosine. Rf in acid eluent A is 0.58, in basic eluent B is 0.35. Same spectrum as for compound 1.

EXAMPLE 8

Synthesis of 8-(5-thioacetamido-fluorescein)-guanosine

The working conditions of Example 1 were applied but substituting 8-bromo-guanosine- for 8-bromo-guanosine-3',5'-(cyclic) phosphate. Rf in solvent A is 0.78 and in solvent B is 0.54.

EXAMPLE 9

Synthesis of 8-(5-thiacetamido-erythrosin)-3',5'-(cyclic) phosphate-guanosine

This compound is obtained by direct iodination of the corresponding compound 1 namely 8-(5-thioacetamido-fluorescein)-3',5'-(cyclic) phospate-guanosine. 4 micromoles of compound 1 in 2 ml of 0.2 nM $NH_3$ were treated with 20 micromoles of iodine dissolved in 2 ml of methanol for 10 hours in room light. The orange coloured product was isolated by chromatography as in Example 1. Rf in solvent A is 0.75, in solvent B is 0.45.

Absorbance maximum in water at pH 9 is at 520 nm. Phosphorescent product.

EXAMPLE 10

Synthesis of 8-(5-thioacetamido-eosin)-3',5'-(cyclic) phosphate-guanosine

The working conditions of example 9 were applied but substituting bromin for iodine. Same Rf. Absorbance maximum in water at pH 9 is at 510 nm. Fluorescent.

EXAMPLE 11 p.methylbenzylphosphate ester of 8-(5-thioacetamido-fluorescein)-3',5' (cyclic) phospate-guanosine This is an example of a phosphate triester obtained by reacting 8-(5-thioacetamido-fluorescein)-3',5'-(cyclic) phosphate-guanosine with a substituted diazomethane (Engel et al., 1977, J. Med. Chem. 20, 907). 5 mg of the compound of Example 1 in the form of triethylamine salt, in 0.5 ml of absolute ethanol were treated with 0.5 ml of tolyldiyomethane (Closs and Moss, J. Am. Chem. Soc. 86, 4042) in darkness for 10 hours. The reaction mixture was separated by silica gel thin layer chromatography with solvent C (chloroform, methanol 6/1 v/v). The fluorescent bands with Rf 0.67 and 0.72 were eluted with methanol and stored at low temperature in solution. The two products were assigned to two isomers (loc. cit.). Rf in solvents A and B, is zero. The ester decomposes rapidly at room temperature and in alkali. This product is an unstable hydrophobic form of the compound of Example 1, into which it spontaneously reconverts. It may be used to introduce the fluorescent cyclic nucleotide across the membrane.

We claim:

1. Biologically active cyclic nucleotides made fluorescent by inserting a fluorescent group, represented by the formula:

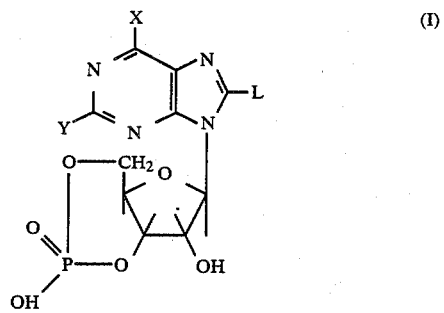

wherein:

X is OH or $NH_2$, Y is $NH_2$ when X=OH and is H when X=$NH_2$ and L is a fluorescent group selected from: 5-thioacetamido-fluorescein, 6-thioacetamido-fluorescein, 5-thioacetamido-2',4',5',7'-tetrabromofluorescein, 6-thioacetamido-2',4',5',7'-tetrabromofluorescein, 5-thioacetamido-2',4',5',7'-tetraiodo-fluorescein, 6-thioacetamido-2',4',5',7'-tetraiodofluorescein, 5-(2-thioacetamido-ethyl)-amino-naphthalene-1-sulphonic acid, and 8-(2-thioacetamido-ethyl)-amino-naphthalene-1-sulphonic acid.

2. The compound of claim 1 wherein X=OH, Y=$NH_2$ and L is 5(thioacetamido)-fluorescein.

3. The compound of claim 1 wherein X=$NH_2$ Y=H and L is 5(thioacetamido)-fluorescein.

4. The compound of claim 1 wherein X=OH, Y=$NH_2$ and L is 5(2-thioacetamido-ethyl)-amino-naphthalene-1-sulphonic acid.

5. The compound of claim 1 wherein X=$NH_2$, Y=H and L is 5(2 thioacetamido-ethyl)-amino-naphthalene-1-sulphonic acid.

6. The compound of claim 1 wherein X=OH, Y=$NH_2$ and L is 6(thioacetamido)-fluorescein.

7. The compound of claim 1 wherein X=$NH_2$, Y=H and L is 6(thioacetamido)-fluorescein.

8. The compound of claim 1 wherein X=OH Y=$NH_2$ and L is 8(2-thioacetamido-ethyl)-amino-naphthalene-1-sulphonic acid.

9. The compound of claim 1 wherein X=$NH_2$ Y=H and L is 8-(2-thioacetamido-ethyl)-amino-naphthalene-1-sulphonic acid.

10. The compound of claim 1 wherein L is 5 (thioacetamido)-2',4',5',7'-tetrabormofluorescein.

11. The compound of claim 1 wherein L is 5(thioacetamido)-2'4'5'7'-tetraiodo-fluorescein.

* * * * *